(12) United States Patent
Pyo et al.

(10) Patent No.: US 8,760,646 B2
(45) Date of Patent: Jun. 24, 2014

(54) METHOD AND APPARATUS FOR MEASURING SIZE OF MICROPARTICLES

(75) Inventors: Hyeon-Bong Pyo, Daejeon (KR); Moon Youn Jung, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 164 days.

(21) Appl. No.: 13/289,396

(22) Filed: Nov. 4, 2011

(65) Prior Publication Data

US 2012/0162643 A1 Jun. 28, 2012

(30) Foreign Application Priority Data

Dec. 23, 2010 (KR) .......................... 10-2010-0134105

(51) Int. Cl.
*G01J 3/28* (2006.01)
(52) U.S. Cl.
USPC ......................................................... 356/326
(58) Field of Classification Search
USPC ........... 356/326, 338; 435/5; 702/23; 700/54; 324/457
See application file for complete search history.

(56) References Cited

U.S. PATENT DOCUMENTS

| 7,719,682 B2 | 5/2010 | Chamberlin et al. |
| 2008/0284446 A1* | 11/2008 | Wang et al. .................... 324/457 |
| 2009/0222218 A1* | 9/2009 | Chamberlin et al. ........... 702/23 |
| 2010/0105026 A1* | 4/2010 | Bruckl et al. ..................... 435/5 |
| 2010/0231909 A1 | 9/2010 | Trainer |

FOREIGN PATENT DOCUMENTS

KR  1020090049706 A  5/2009

OTHER PUBLICATIONS

Mie Scattering by Chris McLinden (Jul. 22, 1999).*

* cited by examiner

*Primary Examiner* — Tarifur Chowdhury
*Assistant Examiner* — Jamil Ahmed

(57) ABSTRACT

A method for measuring the size of microparticles includes: measuring an extinction spectrum of a medium having microparticles dispersed therein; and calculating average size of the microparticles based on the measured extinction spectrum and the Mie scattering theory.

10 Claims, 3 Drawing Sheets

METHOD AND APPARATUS FOR MEASURING SIZE OF MICROPARTICLES

CROSS-REFERENCES TO RELATED APPLICATIONS

The present application claims priority under 35 U.S.C. 119(a) to Korean Application No. 10-2010-0134105, filed on Dec. 23, 2010, in the Korean intellectual property Office, which is incorporated herein by reference in its entirety set forth in full.

BACKGROUND

Exemplary embodiments of the present invention relate to a method and apparatus for measuring the size of microparticles, and more particularly, to a method and apparatus for measuring the size of microparticles, which is capable of easily measuring the average size of microparticles dispersed in a solution.

In general, microparticles refer to particles which are mixed in a water solution or organic solvent and have a size of 1 μm to 100 μm.

Such microparticles may include hemocytes such as red blood cells, white blood cells, or platelets contained in blood, cells contained in urine, saliva, or spinal fluid, yeasts contained in a fermented food such as beer, bacteria contained in a water solution, cells and impurities contained in a suspension such as nanoplankton, juice, ketchup, or milk, generative cells of mammals, impurities contained in an imperfectly-molten suspension, and various metal crystals or nonmetallic crystals mixed in a water solution or solvent.

The sizes of the micro particles dispersed in such solutions may be utilized as information which is physically or chemically important.

The above-described configuration is a related art for helping an understanding of the present invention, and does not mean a related art which is widely known in the technical field to which the present invention pertains.

SUMMARY

An embodiment of the present invention relates to a method and apparatus for measuring the size of microparticles, which is capable of easily measuring the size of microparticles using the Mie scattering theory and a spectrometer.

In one embodiment, a method for measuring size of microparticles comprises: measuring an extinction spectrum of a medium having microparticles dispersed therein; and calculating average size of the microparticles based on the measured extinction spectrum and the Mie scattering theory.

The step of calculating the average size of the microparticles may include: acquiring a maximum value and a minimum value of extinction efficiency from the extinction spectrum; and calculating the size of the microparticles by associating the maximum value and the minimum value of the extinction efficiency with the Mie scattering theory.

In the step of calculating the size of the microparticles, the size of the microparticles may be calculated by comparing the maximum value and minimum value of the extinction efficiency acquired from the extinction spectrum with a maximum value and a minimum value of extinction efficiency calculated by tuning a size parameter in the Mie scattering theory.

The extinction spectrum may have at least two or more local maximum values and minimum values.

The medium may be at least one of liquid medium, gas medium and solid medium. The liquid medium may include at least one of water and buffer solution, the gas medium may include air, and the solid medium may include at least one of silica and polymer.

The microparticles may be dielectric media including at least one of silica and polystyrene, or metallic particles including at least one of gold and silver.

In another embodiment, an apparatus for measuring the size of microparticles includes: a cuvette cell configured to contain a sample having microparticles dispersed therein; a white light source configured to emit light into the cuvette cell; and a spectrometer configured to measure an extinction spectrum of the particles in the cuvette cell generated by the incidence of the light of the white light source and to acquire a maximum value and a minimum value of extinction efficiency by using the measured extinction spectrum and the Mie scattering theory.

BRIEF DESCRIPTION OF THE DRAWINGS

The above and other aspects, features and other advantages will be more clearly understood from the following detailed description taken in conjunction with the accompanying drawings, in which.

DESCRIPTION OF SPECIFIC EMBODIMENTS

Hereinafter, embodiments of the present invention will be described with reference to accompanying drawings. However, the embodiments are for illustrative purposes only and are not intended to limit the scope of the invention.

The drawings are not necessarily to scale and in some instances, proportions may have been exaggerated in order to clearly illustrate features of the embodiments. Furthermore, terms to be described below have been defined by considering functions in embodiments of the present invention, and may be defined differently depending on a user or operator's intention or practice. Therefore, the definitions of such terms are based on the descriptions of the entire present specification.

Figure 1:
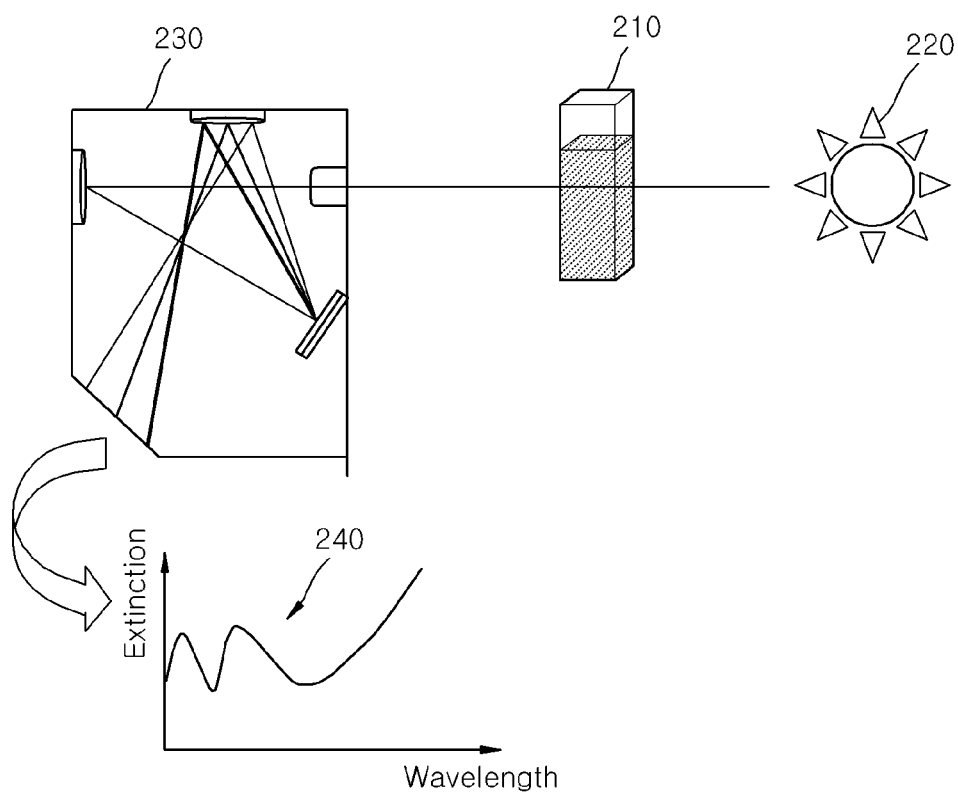
FIG. 1 is a diagram explaining a method and apparatus for measuring the size of microparticles in accordance with an embodiment of the present invention.
Figure 2:
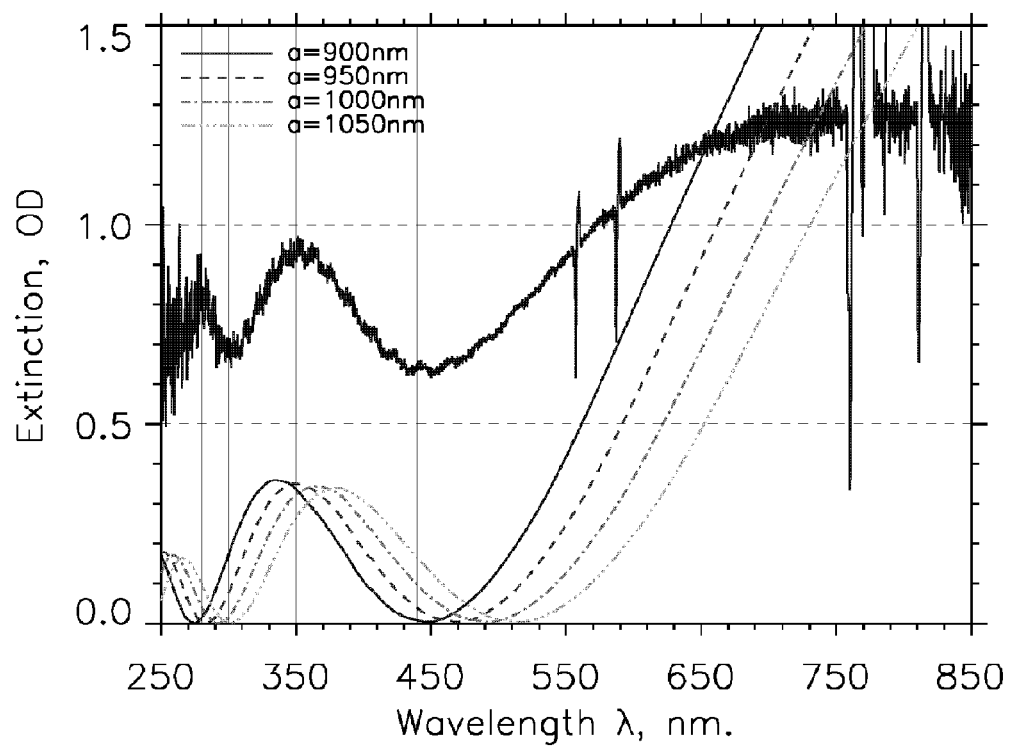
FIG. 2 is a diagram showing an extinction spectrum in accordance with the embodiment of the present invention.

FIG. 1 is a diagram explaining a method and apparatus for measuring the size of microparticles in accordance with an embodiment of the present invention, and FIG. 2 is a diagram showing an extinction spectrum in accordance with the embodiment of the present invention.

Referring to FIG. 1, the apparatus for measuring the size of microparticles in accordance with the embodiment of the present invention includes a cuvette cell 210, a white light source 220, and a spectrometer 230.

The cuvette cell 210 contains a solution in which microparticles to be measured are dispersed.

The white light source 220 emits light into the cuvette cell 210 containing the solution having the microparticles dispersed therein.

The spectrometer 230 is an analysis instrument of a sample contained in the cuvette cell 210 and serves to detect an extinction spectrum 240 of the solution having the microparticles dispersed therein, generated by the incidence of the light.

A sample extinction spectrum obtained from the sample by the spectrometer 230 and a reference extinction spectrum obtained from a reference sample are used to determine an optical density (OD) according to the Beer-Lambert law.

Then, the optical density is expressed as extinction efficiency $Q_{EXT}$ as a function of the wavelength.

Referring to FIG. 2, in case of transparent dielectric material the extinction spectrum 240 exhibits an interference pattern having at least a maximum value and a minimum value.

The optical density on the y axis represents a value of extinction efficiency calculated according to the Beer-Lambert law, and an offset value of the optical density may differ depending on the molar concentration of the solution.

The following equation is used to calculate the extinction efficiency based on the Mie scattering theory.

$$Q_{EXT} = \frac{2}{(ka)^2} \sum_{n=1}^{\infty} (2n+1)\{Re(a_n + b_n)\}$$

$$a_n = \frac{m\psi_n(mx)\psi_n'(x) - \psi_n(x)\psi_n'(mx)}{m\psi_n(mx)\xi_n'(x) - \xi_n(x)\psi_n'(mx)}$$

$$b_n = \frac{\psi_n(mx)\psi_n'(x) - m\psi_n(x)\psi_n'(mx)}{\psi_n(mx)\xi_n'(x) - m\xi_n(x)\psi_n'(mx)},$$

$$\psi_n(x) = xj_n(x), \quad \xi_n(x) = xh_n^{(1)}(x)$$

$$x = ka = \frac{2\pi a}{\lambda}, \quad m = \frac{N_p}{N_h} = \frac{RI \text{ of the particles}}{RI \text{ of the host matrix}}$$

Referring to the equation, the extinction efficiency $Q_{EXT}$ may be calculated from scattering coefficients $a_n$ and $b_n$, a wavelength λ, or wave vector k, and the radius of the microparticles a.

Here, x is a size parameter as a function of the wavelength. m is a ratio of a dispersion function, namely (n,k) data or equivalently, a ratio of refractive indices of the microparticles and surrounding medium, respectively. $j_n(x)$ and $h^{(1)}{}_n(x)$ represent the Riccati-Bessel function and the Riccati-Hankel function, respectively. RI represents refractive index.

The maximum value and the minimum value of the extinction efficiency as a function of the wavelength correspond to the size of the microparticles a, when dielectric function, namely the refractive index and extinction coefficient (n,k) of the microparticles and the solution are given.

Therefore, when the maximum value and the minimum value of the extinction efficiency which is calculated by controlling the size parameter x in the equation for calculating the extinction efficiency based on the Mie scattering theory are associated with experimental values, the size a of the microparticles may be measured.

Figure 3:
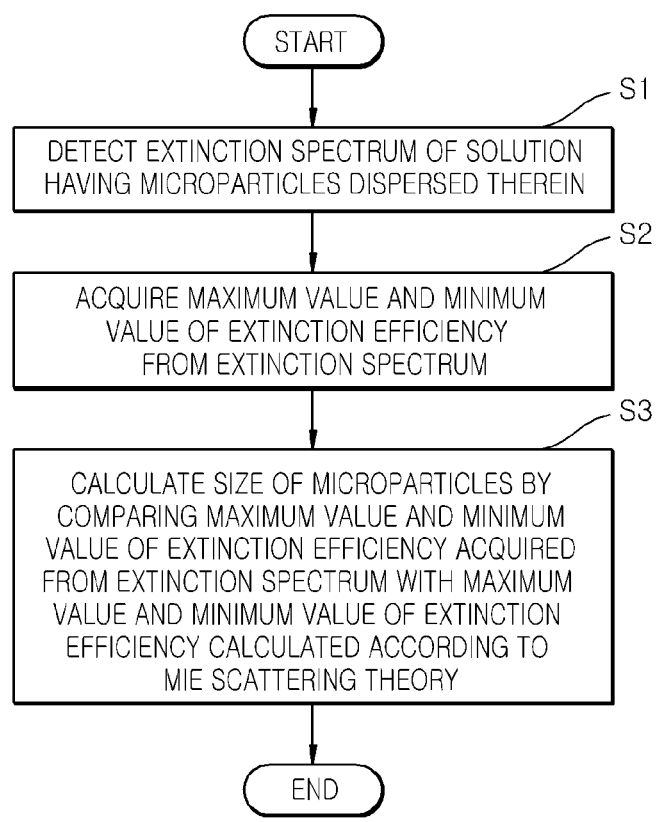
FIG. 3 is a flow chart for explaining the method for measuring the size of microparticles in accordance with the embodiment of the present invention.

FIG. 3 is a flow chart for explaining the method for measuring the size of microparticles in accordance with the embodiment of the present invention.

Referring to FIG. 3, light is incident on the cuvette cell 210 to measure an extinction spectrum 240 of a solution having microparticles dispersed therein through the spectrometer 230, at step S1.

Then, a maximum value and a minimum value of extinction efficiency are obtained from the measured extinction spectrum at step S2.

Typically, the extinction spectrum is represented by optical density OD, and the extinction efficiency has the following relation: OD=$Q_{EXT}$*n*d. Here, n represents the molar concentration of microparticles, and d represents the path length of light.

Next, the average size of the microparticles is calculated by comparing the maximum value and the minimum value of the extinction efficiency acquired from the extinction spectrum with the maximum value and the minimum value of the extinction efficiency which is calculated by tuning the size parameter in the Mie scattering theory, at step S3.

As such, the method and apparatus in accordance with the embodiment of the present invention may easily determine the size of microparticles which are dispersed in a solution, by using the Mie scattering theory and the spectrometer.

The medium may be at least one of liquid medium, gas medium and solid medium. The liquid medium may include at least one of water and buffer solution, the gas medium may include air, and the solid medium may include at least one of silica and polymer.

The embodiments of the present invention have been disclosed above for illustrative purposes. Those skilled in the art will appreciate that various modifications, additions and substitutions are possible, without departing from the scope and spirit of the invention as disclosed in the accompanying claims.

What is claimed is:

1. A method for measuring size of microparticles, comprising:

measuring, by a spectrometer, an extinction spectrum of a medium having microparticles dispersed therein; and calculating average size of the microparticles based on the measured extinction spectrum and the Mie scattering theory, by obtaining a maximum value and a minimum value of extinction efficiency from the extinction spectrum, and calculating the size of the microparticles by associating the maximum value and the minimum value of the extinction efficiency with the calculated extinction efficiency based on the Mie scattering theory, wherein the following equations are used by the spectrometer to calculate the extinction efficiency based on the Mie scattering theory $$Q_{EXT} = \frac{2}{(ka)^2} \sum_{n=1}^{\infty} (2n+1)\{Re(a_n + b_n)\}$$

$$a_n = \frac{m\psi_n(mx)\psi_n'(x) - \psi_n(x)\psi_n'(mx)}{m\psi_n(mx)\xi_n'(x) - \xi_n(x)\psi_n'(mx)}$$

$$b_n = \frac{\psi_n(mx)\psi_n'(x) - m\psi_n(x)\psi_n'(mx)}{\psi_n(mx)\xi_n'(x) - m\xi_n(x)\psi_n'(mx)},$$

$$\psi_n(x) = xj_n(x), \quad \xi_n(x) = xh_n^{(1)}(x)$$

$$x = ka = \frac{2\pi a}{\lambda}, \quad m = \frac{N_p}{N_h} = \frac{RI \text{ of the particles}}{RI \text{ of the host matrix}}$$

wherein an and bn are scattering coefficients, is a wavelength, k is a wave vector, a is the radius of a microparticle, m is a ratio of the refractive indices of the microparticles and surrounding medium, and $j_n(x)$ and $h^{(1)}{}_n(x)$ represent the Riccati-Bessel function and the Riccati-Hankel function, respectively, RI represents refractive index, and x represents a size parameter for (n, k) data.

2. The method of claim 1, wherein, in the step of calculating the size of the microparticles, the size of the microparticles is calculated by comparing the maximum value and minimum value of the extinction efficiency obtained from the extinction spectrum with a maximum value and a minimum value of extinction efficiency calculated by tuning a size parameter based on the Mie scattering theory.

3. The method of claim 2, wherein the extinction spectrum has at least two or more local maximum values and minimum values.

4. The method of claim 1, wherein the medium is at least one of liquid medium, gas medium and solid medium, and
wherein the liquid medium includes at least one of water and
buffer, the gas medium includes air, and the solid medium includes at least one of silica and polymer.

5. The method of claim 1, wherein the microparticles are dielectric media including at least one of silica and polystyrene, or metallic particles including at least one of gold and silver.

6. An apparatus for measuring the size of microparticles, comprising:
a cuvette cell configured to contain a medium having microparticles dispersed therein;
a white light source configured to emit light into the cuvette cell; and
a spectrometer configured to measure an extinction spectrum of the particles in the cuvette cell generated by the incidence of the light of the white light source and to acquire a maximum value and a minimum value of extinction efficiency by using the measured extinction spectrum and the Mie scattering theory, wherein the spectrometer is configured to
obtain a maximum value and a minimum value of extinction efficiency from the extinction spectrum, and
calculate the size of the microparticles by associating the maximum value and the minimum value of the extinction efficiency with the calculated extinction efficiency based on the Mie scattering theory,
wherein the following equations are used by the spectrometer to calculate the extinction efficiency based on the Mie scattering theory $$Q_{EXT} = \frac{2}{(ka)^2} \sum_{n=1}^{\infty} (2n+1)\{Re(a_n + b_n)\}$$

$$a_n = \frac{m\psi_n(mx)\psi'_n(x) - \psi_n(x)\psi'_n(mx)}{m\psi_n(mx)\xi'_n(x) - \xi_n(x)\psi'_n(mx)}$$

$$b_n = \frac{\psi_n(mx)\psi'_n(x) - m\psi_n(x)\psi'_n(mx)}{\psi_n(mx)\xi'_n(x) - m\xi_n(x)\psi'_n(mx)},$$

$$\psi_n(x) = x j_n(x), \quad \xi_n(x) = x h_n^{(1)}(x)$$

$$x = ka = \frac{2\pi a}{\lambda}, \quad m = \frac{N_p}{N_h} = \frac{RI \text{ of the particles}}{RI \text{ of the host matrix}}$$

wherein $a_n$ and $b_n$ are scattering coefficients, is a wavelength, k is a wave vector, a is the radius of a microparticle, m is a ratio of the refractive indices of the microparticles and surrounding medium, and $j_n(x)$ and $h^{(1)}_n(x)$ represent the Riccati-Bessel function and the Riccati-Hankel function, respectively, RI represents refractive index, and x represents a size parameter for (n, k) data.

7. The apparatus of claim 6, wherein the spectrometer calculates the size of the microparticles by comparing the maximum value and minimum value of the extinction efficiency obtained from the extinction spectrum with a maximum value and a minimum value of extinction efficiency calculated by tuning a size parameter based on the Mie scattering theory.

8. The apparatus of claim 7, wherein the extinction spectrum has at least two or more local maximum values and minimum values.

9. The apparatus of claim 6, wherein the medium is at least one of liquid medium, gas medium and solid medium, and
wherein the liquid medium includes at least one of water and
buffer, the gas medium includes air, and the solid medium includes at least one of silica and polymer.

10. The method of claim 6, wherein the microparticles are dielectric media including at least one of silica and polystyrene, or metallic particles including at least one of gold and silver.

* * * * *